(12) United States Patent
Howe et al.

(10) Patent No.: US 8,696,991 B1
(45) Date of Patent: Apr. 15, 2014

(54) FIELD DEPLOYABLE SURFACE PLASMON RESONANCE BASED BIOSENSOR

(76) Inventors: Harold W. Howe, Butte, MT (US);
Timothy S. Troutman, Butte, MT (US);
Michael E. Meichle, Butte, MT (US);
Adrian L. Krag, Santa Clarita, CA (US)

( * ) Notice: Subject to any disclaimer, the term of this patent is extended or adjusted under 35 U.S.C. 154(b) by 336 days.

(21) Appl. No.: 12/930,340

(22) Filed: Jan. 4, 2011

Related U.S. Application Data

(60) Provisional application No. 61/335,297, filed on Jan. 4, 2010.

(51) Int. Cl.
*G01N 21/00* (2006.01)

(52) U.S. Cl.
USPC .......... 422/82.05; 422/50; 422/400; 422/401; 422/402; 422/403; 422/404; 422/82.08; 422/82.09; 422/501; 422/502; 436/172; 436/174; 436/180; 435/287.1; 435/288.7

(58) Field of Classification Search
USPC ............... 422/50, 400–404, 430, 68.1, 82.05, 422/82.08–82.09, 500–502, 565; 436/164–165, 172, 174, 180; 435/283.1, 287.1–288.7, 4–7.2
See application file for complete search history.

(56) References Cited

U.S. PATENT DOCUMENTS

| | | | |
|---|---|---|---|
| 3,656,833 A | 4/1972 | Wallace | |
| 4,931,402 A | 6/1990 | Abplanalp | |
| 5,156,976 A | 10/1992 | Slovacek et al. | |
| 5,209,904 A | 5/1993 | Forney et al. | |
| 5,607,643 A | 3/1997 | Xiaoming et al. | |
| 5,912,456 A | 6/1999 | Melendez et al. | |
| 6,432,364 B1 | 8/2002 | Negami et al. | |
| 6,611,367 B1 | 8/2003 | Naya et al. | |
| 6,756,223 B2 | 6/2004 | Roberts et al. | |
| 6,870,627 B2 | 3/2005 | Elkind et al. | |
| 6,956,695 B2 | 10/2005 | Tafas et al. | |
| 7,307,730 B2 | 12/2007 | Sarvazyan et al. | |
| 7,333,197 B2 | 2/2008 | Fritz et al. | |
| 7,554,657 B2 | 6/2009 | Bosio | |
| 7,738,934 B2 | 6/2010 | Takase et al. | |
| 7,842,242 B2 | 11/2010 | Dickopf et al. | |
| 7,842,247 B2 | 11/2010 | Maurer et al. | |
| 2003/0003018 A1 | 1/2003 | Stolowitz et al. | |
| 2003/0206708 A1 | 11/2003 | Estes et al. | |
| 2006/0188401 A1 | 8/2006 | Robotti et al. | |
| 2006/0279737 A1* | 12/2006 | Chinowsky et al. | 356/445 |
| 2007/0222998 A1 | 9/2007 | Sasaki et al. | |
| 2007/0279634 A1 | 12/2007 | Gruhlke et al. | |

(Continued)

FOREIGN PATENT DOCUMENTS

| | | |
|---|---|---|
| TW | 249768 | 2/2006 |
| WO | WO 2008/007115 | 1/2008 |
| WO | WO 2009/022985 | 2/2008 |
| WO | WO 2008094285 A2 * | 8/2008 |

*Primary Examiner* — Lyle Alexander
(74) *Attorney, Agent, or Firm* — Robert M Hunter

(57) ABSTRACT

An apparatus and method for detection of anything to which an antibody can be raised, or to which a chemical receptor can be fashioned, based on surface plasmon resonance. The apparatus and method have the capability to detect proteins, viruses, bacteria, toxins, pathogens, contaminants, chemical compounds, or nucleic acids based on surface plasmon resonance and surface receptor technologies which may include antibodies or chemical receptors. The device is field deployable and utilizes a single use sample holder card which includes the sample to be tested, test channels, waste reservoir and a functionalized test surface.

11 Claims, 12 Drawing Sheets

(56) References Cited

U.S. PATENT DOCUMENTS

| | | | |
|---|---|---|---|
| 2007/0292941 A1* | 12/2007 | Handique et al. | 435/288.7 |
| 2008/0085213 A1* | 4/2008 | Wu et al. | 422/68.1 |
| 2008/0182301 A1* | 7/2008 | Handique et al. | 435/91.2 |
| 2009/0103099 A1 | 4/2009 | Debackere et al. | |
| 2009/0303489 A1 | 12/2009 | Allsop et al. | |
| 2010/0096561 A1 | 4/2010 | Johnson et al. | |
| 2010/0103421 A1 | 4/2010 | Johansen et al. | |
| 2010/0150781 A1 | 6/2010 | Ervin et al. | |
| 2010/0216975 A1 | 8/2010 | Wu et al. | |
| 2010/0284012 A1 | 11/2010 | Chinowsky et al. | |
| 2012/0135511 A1* | 5/2012 | Battrell et al. | 435/287.2 |

* cited by examiner

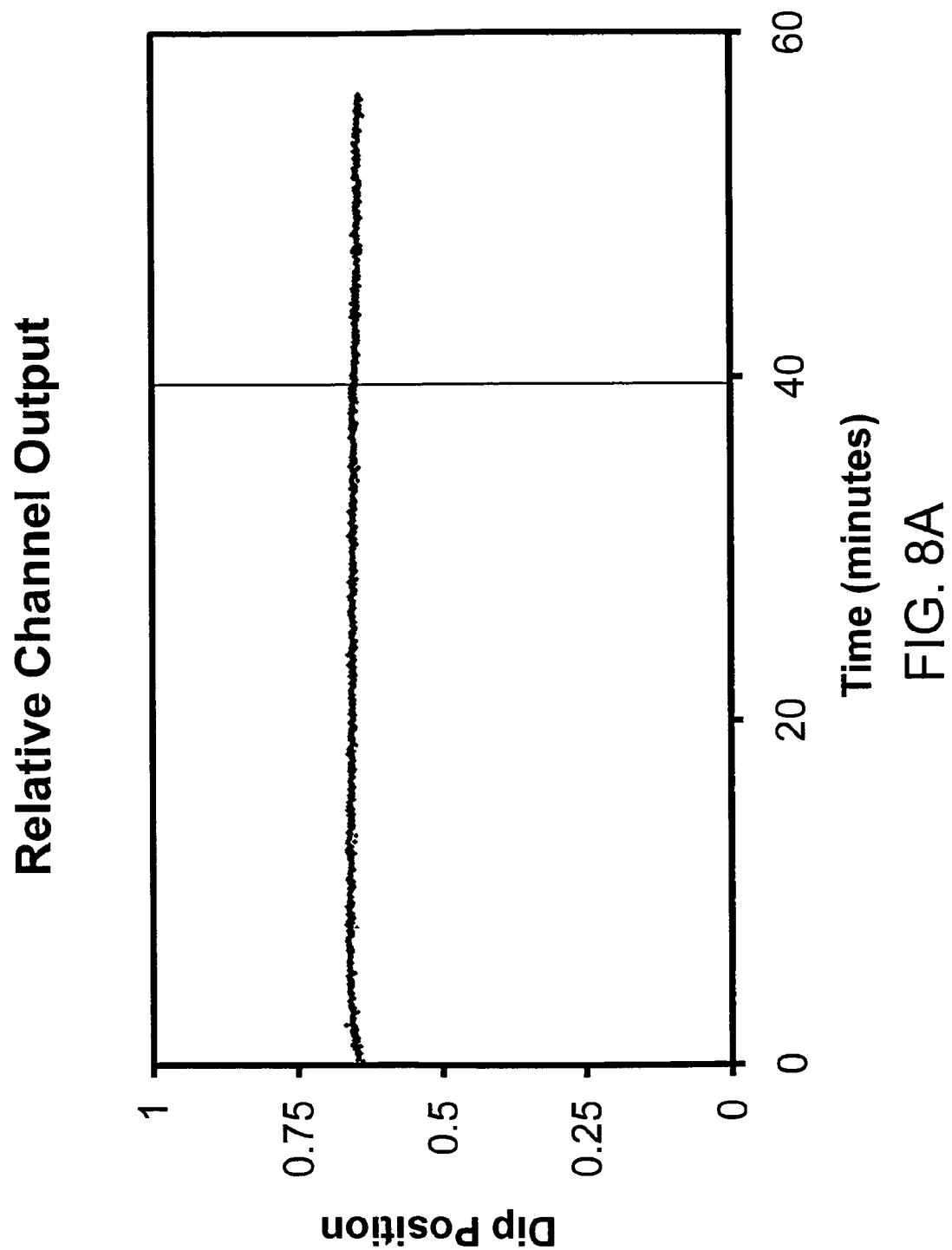

FIELD DEPLOYABLE SURFACE PLASMON RESONANCE BASED BIOSENSOR

CROSS-REFERENCES TO RELATED APPLICATIONS

This application claims the benefit of U.S. Provisional Patent Application No. 61/335,297 filed Jan. 4, 2010, the disclosure of which patent application is incorporated by reference as if fully set forth herein.

STATEMENT REGARDING FEDERALLY SPONSORED RESEARCH OR DEVELOPMENT

The U.S. Government has a paid-up license in this invention and the right in limited circumstances to require the patent owner to license others on reasonable terms as provided for by the terms of Grant No. W81XWH-06-1-0275 awarded by the United States Army.

THE NAMES OF THE PARTIES TO A JOINT RESEARCH AGREEMENT

Not Applicable

INCORPORATION-BY-REFERENCE OF MATERIAL SUBMITTED ON A COMPACT DISC

Not Applicable

BACKGROUND OF THE INVENTION

This invention relates to testing in the fields of chemistry, biology, and biotechnology. In particular, the invention relates to testing for pathogens and other analytes using a surface plasmon resonance (SPR) process.

Surface plasmon resonance (SPR) is a powerful analytical principle which is very sensitive to changes on an interrogated surface. Surface plasmons are generated in certain metals when light is incident upon the prism metal interface at a specific angle. As the properties of the surface change, e.g., the binding of a molecule to the surface, the angle at which SPR occurs is measurably shifted. The presence of a surface plasmon reduces the amount of light reflected at the specific angle, so a binding event on the surface results in a direct translation of the reflection minima: a parameter that is readily measurable.

In the background art, instruments utilizing SPR as a method of detection have been limited to laboratory use due to bulky size, limited field portability, and complicated operating procedures. Despite their shortcomings, SPR instruments are highly sensitive to extremely small changes at the interrogated surface. This makes the principle ideal for ultra-trace level detection. What is needed, however, is a compact detection system, with a simple user interface and operation, as well as pre-functionalized surfaces which together limit the required user skills to pressing buttons, performing simple sample injections upon prompting, and reading the result from a screen.

The Spreeta™ SPR transducer is an inexpensive SPR transducer that was originally developed by Texas Instruments, Inc. and is currently manufactured by Sensata Technologies, Inc. of Attleboro, Mass. The Spreeta™ SPR transducer has become competitive with other SPR methods and instruments, rivaling other SPR-based designs. The Spreeta™ SPR transducer contains a light source, prism, and a charge-coupled device (CCD) to generate light, interrogate the active surface at multiple angles, and recover the reflection signal of SPR respectively. Electronic circuitry drives the Spreeta™ SPR transducer, as well as extracts and analyzes the signal it produces to characterize the SPR result and determine whether a compound of interest is present. On the face of the Spreeta™ SPR transducer, a single use functionalized chip bears the plasmon-generating metal as the active, interrogated surface and the self-contained fluidics portion of a chip into which the sample is injected and retained.

The SPR technique is readily sensitive to mass changes well below the level of nanograms per milliliter without the benefit of secondary labeling techniques. The technique has the ability to use a mass-labeling technique for secondary amplification if necessary to provide additional signal under the condition of a positive binding event. For example, the system will recognize a bound virus, and generate an additional signaling event, allowing for greater sensitivity, improved likelihood of positive identification, and reduction of the lower detection limit.

Though SPR has been developed as a technology over the past 20 years, it is still being advanced through physical and computational means. Faster processing with modern hardware allows for a more compact electronics package, enabling portability, as well as faster sampling rates and resultant smoothness and reliability of signal.

In the physical interactions which take place on the active SPR surface, there are other advancements in the form of surface modification, perhaps most notably in the realm of nanoparticle labeling and nanotexturing of surfaces. This incorporation of nanotechnology with SPR is still in a very experimental state, but shows promise to improve the detection limits of the technique. SPR technology has largely been limited to laboratory use, where it provides high-sensitivity, high-specificity molecular identification and is utilized in sample testing for the presence of cells, viruses, biomolecules, nucleic acids and other compounds.

The background art is characterized by U.S. Pat. Nos. 3,656,833; 4,931,402; 5,156,976; 5,209,904; 5,607,643; 5,912,456; 6,432,364; 6,611,367; 6,756,223; 6,870,627; 6,956,695; 7,307,730; 7,333,197; 7,554,657; 7,738,934; 7,842,242; and 7,842,247; and U.S. Patent Application Nos. 2003/0003018; 2003/0206708; 2006/0188401; 2007/0222998; 2007/0279634; 2009/0103099; 2009/0303489; 2010/0096561; 2010/0103421; 2010/0150781; 2010/0216975; and 2010/0284012; the disclosures of which patents and patent applications are incorporated by reference as if fully set forth herein. The background art is also characterized by the following patents and patent applications: TW 249768; WO 2008/007115; and WO/2009/022985.

BRIEF SUMMARY OF THE INVENTION

As used herein, the following terms and variations thereof have the meanings given below, unless a different meaning is clearly intended by the context in which such term is used.

"A," "an" and "the" and similar referents used herein are to be construed to cover both the singular and the plural unless their usage in context indicates otherwise.

"About" means within five percent of a recited parameter or measurement, and preferably within one percent of such parameter or measurement.

"Comprise" and variations of the term, such as "comprising" and "comprises," are not intended to exclude other additives, components, integers or steps.

"Exemplary," "illustrative," and "preferred" mean "another."

"Horizontal" means substantially parallel to the orientation of the card insertion slot.

"Vertical" means substantially perpendicular to the orientation of the card insertion slot.

In an illustrative embodiment, the invention offers this powerful recognition technology in a standalone platform for sample testing in the field. In this embodiment, the invention provides a solution for detection of chemical and biological agents (e.g., vector-borne viruses) which utilizes a field-portable, SPR-based detector. A battery powered instrument receives a single-use sensor card that is specifically functionalized for the target of interest. These sensor cards are capable of being prepared so that they can test for multiple analytes simultaneously.

In an illustrative embodiment, the invention is a sensor comprising: a housing having a card slot, a heat sink opening, a knob opening and a display opening; an integrated surface plasmon resonance transducer comprising a light source and a polarizer for producing polarized light, a light transmissive window for transmitting said polarized light and a reflection of said polarized light, a mirrored surface for directing said reflection, and a detector array for detecting said reflection, said integrated surface plasmon resonance transducer being disposed within said housing; a functionalized card disposed in said card slot, said functionalized card comprising a body having an upper wall having an upper outer surface and a lower wall having lower outer surface and a microfluidic channel having a sample input port that is provided with a septum, a sample input reservoir that is in fluid communication with said sample input port, a test channel and a reference channel that are in fluid communication with said sample input reservoir, a waste reservoir that is in fluid communication with said test channel and said reference channel, a hydrophobic filter that is in fluid communication with said waste reservoir, a vacuum output port that is in fluid communication with said hydrophobic filter and a chip having a metallic test surface that forms an interior wall of said test channel and an inner wall of said reference channel for producing said reflection; an index matching fluid disposed between said light transmissive window and said lower outer surface and adjacent to said metallic test surface; a card holding mechanism for positioning said functionalized card against said integrated surface plasmon resonance transducer so that said test channel and said metallic test surface are exposed to said polarized light and so that said detector array is exposed to said reflection, said card holding mechanism comprising a spring that is operative to urge said functionalized card toward said integrated surface plasmon resonance transducer and a card releasing mechanism comprising a knob that is disposed in said knob opening, a drive shaft that is attached to said knob, a spur gear that is attached to said drive shaft, a rack gear for engaging with said spur gear, a horizontally movable wedge for engaging with said rack gear and a vertically movable wedge for engaging with said horizontally movable wedge and with said card, said card releasing mechanism being operative to reverse the motion urged by said spring when said knob is rotated; a heat storage component that is disposed adjacent to said functionalized card and is in contact with said upper outer surface, said heat storage component having a thermistor well, an insulation layer that is disposed adjacent to said heat storage component, a heat sink that is disposed in said heat sink opening, said heat sink having a cavity that is disposed adjacent to said insulation layer, a heating and cooling device that is disposed adjacent to said heat storage component and in said cavity, and a thermistor that is disposed in said thermistor well; a vacuum pump that is in fluid communication with said vacuum output port that is operative to move a sample that has been injected into said sample input port through said microfluidic channel, said vacuum pump being disposed in said housing; a power source that is disposed within said housing; a plurality of control switches that are mounted on said housing; a control circuit interface board that is disposed within said housing; a computer/controller that is disposed within said housing, said computer/controller being operative to receive signals from said thermistor and control the temperature of said heat storage component and to process signals from said integrated surface plasmon resonance transducer and to produce an output; and a display that is mounted in said display opening and that is operative to receive and display said output. In another embodiment, said heating and cooling device comprises: a Peltier assembly. In another embodiment, said functionalized card further comprises: a top cover layer that provides a top for said sample input reservoir and said waste reservoir and that holds said septum and said filter in said functionalized card; a septum spacer layer that contains said septum; a first adhesive layer that joins said top cover layer and said septum spacer layer; a filter spacer layer that contains said filter; a second adhesive layer that joins said septum spacer layer and said filter spacer layer; a reservoir layer in which sample input reservoir and said waste reservoir are formed; a third adhesive layer that joins said filter spacer layer and said reservoir layer; a bottom cover layer that provides a bottom for said sample input reservoir and said waste reservoir; and a fourth adhesive layer that joins said reservoir layer and said bottom cover layer. In another embodiment, said interior wall is functionalized and said inner wall is not.

In another illustrative embodiment, the invention is a surface plasmon resonance analytical kit comprising: means for measuring a surface plasmon resonance comprising an integrated surface plasmon resonance transducer that produces a signal; a functionalized card comprising a microfluidic system having a test channel active surface and a reference channel active surface, said functionalized card being adapted to receive a sample; means for holding said functionalized card in optical communication with said integrated surface plasmon resonance transducer, said means for holding comprising elastic members that exert forces that urge said functionalized card toward said integral surface plasmon resonance transducer; means for releasing said functionalized card comprising a rack and pinion that are operative to overcome said forces and allow said functionalized card to move away from said integral surface plasmon transducer; and means for processing said signal to produce an indication of whether said sample contains an analyte of interest.

In another illustrative embodiment, the invention is a method for detecting the presence or amount of an analyte in a sample using a biosensor that comprises a card holding mechanism, a thermal mass and a surface plasmon resonance transducer, said method comprising: introducing the sample into a functionalized card, said functionalized card having a waste reservoir, an exit port, a reference channel having a reference channel active surface, and a test channel that is functionalized to retain the analyte on a test channel active surface; rotating an actuator in a first direction that rotates a pinion that moves a rack and a horizontally movable wedge that moves a vertically movable wedge which moves the card holding mechanism to a card receiving position; applying an index matching fluid or conformal coating to said functionalized card and inserting said functionalized card into the biosensor at a location that is adjacent to the thermal mass; rotating said actuator in a second direction that rotates said pinion that moves said rack and said horizontally movable wedge that moves said vertically movable wedge which moves the card holding mechanism to a card holding position with said functionalized card being held against the surface plasmon resonance transducer and in thermal communication with said thermal mass; controlling the temperature of said functionalized card at a set point by measuring a temperature of said thermal mass and heating or cooling said thermal mass; imposing a vacuum on said exit port to move said sample from said sample input reservoir through said test channel and said reference channel into said waste reservoir; measuring a first surface plasmon resonance signal emitted by said test channel active surface and a second surface plasmon resonance signal emitted by said reference channel active surface to produce a test signal and a control signal; and processing said test signal and said control signal in a processor to produce an indication of the presence of the analyte. In another embodiment, the method further comprises: processing said test signal and said control signal in a processor to produce a concentration of the analyte in the sample. In another embodiment, the method further comprises: imposing a pressure difference is operative to produce a flow rate of 20 to 40 microliters per minute across said functionalized card. In another embodiment, controlling the temperature of said functionalized card step comprises use of a proportional stage, an integrator stage and a differentiator stage. In another embodiment, controlling the temperature of said functionalized card is operative to stabilize the temperature of said functionalized card to within 0.15 degrees C. over a sixty minute period.

In a further illustrative embodiment, the invention is a method for detecting the presence or amount of an analyte in a sample using a biosensor that comprises a thermal mass, a card holding mechanism and a surface plasmon resonance transducer, said method comprising: a step for introducing the sample into a functionalized card, said functionalized card having a sample reservoir, a reference channel having a reference channel active surface, a waste reservoir, a hydrophobic filter, an exit port and a test channel that is functionalized to retain the analyte on a test channel active surface; a step for rotating an actuator of the card holding mechanism in a first direction that rotates a pinion that moves a rack to a card receiving position; a step for applying an index matching fluid to said functionalized card and inserting said functionalized card into said biosensor at a location that is adjacent to the thermal mass; a step for rotating said actuator of the card holding mechanism in a second direction that rotates said pinion that moves said rack to a card holding position with said functionalized card being held in optical communication with the surface plasmon resonance transducer and in thermal communication with the thermal mass; a step for controlling the temperature of said functionalized card by measuring a temperature of the thermal mass and heating or cooling the thermal mass; a step for imposing a vacuum on said exit port to move said sample from said sample reservoir through said test channel and into said waste reservoir; a step for measuring a first surface plasmon resonance of said test channel active surface and a second surface plasmon resonance of said control active surface to produce a test signal and a control signal; and a step for processing said test signal and said control signal in a processor to produce an indication of the presence or absence of the analyte. In another embodiment, the method further comprises: a step for processing said test signal and said control signal in a processor to produce a concentration of the analyte in the sample. In another embodiment, said step for imposing a pressure difference is operative to produce a flow rate of 20 to 40 microliters per minute across said functionalized card. In another embodiment, said step for controlling the temperature of said functionalized card comprises use of a proportional stage, an integrator stage and a differentiator stage. In another embodiment said step for controlling the temperature of said functionalized card is operative to stabilize the temperature of said functionalized card to within 0.025 degrees C. over a sixty minute period.

In yet another illustrative embodiment, the invention is a system for detecting the presence or amount of an analyte in a sample using a biosensor that comprises a thermal mass, a card holding mechanism and a surface plasmon resonance transducer, said method comprising: means for introducing the sample into a functionalized card, said functionalized card having a sample reservoir, a reference channel having a reference channel active surface, a waste reservoir, a hydroscopic filter, an exit port and a test channel that is functionalized to retain the analyte on a test channel active surface; means for rotating a pinion of said card holding mechanism in a first direction that moves a rack to a card receiving position; means for accepting said functionalized card in a slot that is adjacent to the thermal mass; means for rotating said pinion of said card holding mechanism in a second direction that moves said rack to a card holding position with said functionalized card being held in optical communication with the surface plasmon resonance transducer and in thermal communication with the thermal mass; means for controlling the temperature of said functionalized card by measuring a temperature of the thermal mass and heating or cooling the thermal mass; means for imposing a pressure difference to move the sample from said sample reservoir through said test channel and said reference channel into said waste reservoir; means for measuring a test channel surface plasmon resonance of said test channel active surface and a reference channel surface plasmon resonance of said reference channel active surface to produce a test signal and a control signal; and means for processing said test signal and said control signal in a processor to produce an indication of the presence or absence of the analyte. In another embodiment, the system further comprises: means for processing said test signal and said control signal in a processor to produce a concentration of the analyte in the sample. In another embodiment, said means for imposing a pressure difference is operative to produce a flow rate of 20 to 40 microliters per minute across said functionalized card. In another embodiment, said means for controlling the temperature of said functionalized card comprises a proportional stage, an integrator stage and a differentiator stage. In another embodiment, said means for controlling the temperature of said functionalized card is operative to stabilize the temperature of said functionalized card to within 0.025 degrees C. over a sixty minute period.

In yet another illustrative embodiment, the invention is a field deployable surface plasmon resonance based biosensor comprising: a functionalized card comprising a microfluidic system that delivers a sample to a functionalized test surface chip in a test channel and in a reference channel; a card holding mechanism that comprises springs that hold said functionalized card in a card holding position during a test and a knob, pinion, rack and wedges that are operative to compress said springs when said card holding mechanism is in a card releasing position before and after said test;

a thermal control system that is operative to control the temperature of said functionalized card indirectly by controlling the temperature of a thermal mass that is disposed adjacent to said functionalized card when the card holding mechanism is in the card holding position; an integrated surface plasmon resonance transducer that is operative be in optical communications with said activated test surface chip and is operative to characterize reflections from said activated test surface chip and produce output signals; a processor that is operative to process said output signals; and a user interface comprising switches and a display that is operative to accept input from a user and to present biosensor results to said user. In another embodiment, said thermal control system comprises a Peltier assembly.

Further aspects of the invention will become apparent from consideration of the drawings and the ensuing description of exemplary embodiments of the invention. A person skilled in the art will realize that other embodiments of the invention are possible and that the details of the invention can be modified in a number of respects, all without departing from the concept. Thus, the following drawings and description are to be regarded as illustrative in nature and not restrictive.

BRIEF DESCRIPTION OF THE SEVERAL VIEWS OF THE DRAWINGS

The features of the invention will be better understood by reference to the accompanying drawings which illustrate exemplary embodiments of the invention. In the drawings:

FIG. 8A is a plot of thermal stability achieved with an illustrative embodiment of the field deployable biosensor.

Figure 1:
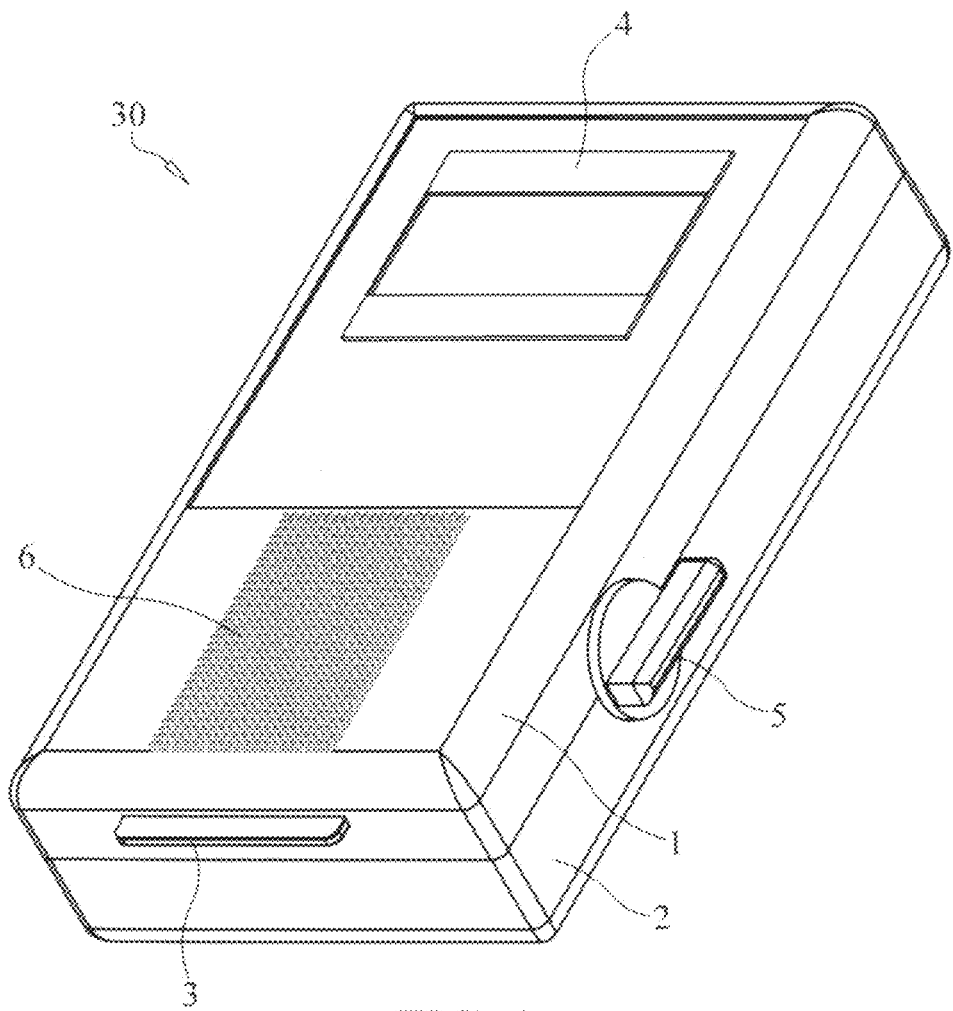
FIG. 1 is a perspective view of an illustrative embodiment of the invention.

The following reference numerals are used to indicate the parts and environment of an illustrative embodiment invention on the drawings:

| | |
|---|---|
| 1 | top cover/housing |
| 2 | bottom cover/housing |
| 3 | horizontal card insertion slot, card insertion slot, slot |
| 4 | display, screen |
| 5 | actuator, knob. |
| 6 | heat sink |
| 7 | control switches |
| 8 | Peltier assembly, heater/cooler |
| 9 | control circuit interface board |

-continued

| | |
|---|---|
| 10 | controller, computer |
| 11 | functionalized, single use card, single use card, card |
| 12 | vacuum pump, pump |
| 13 | heat storage component, thermal reservoir, thermal mass |
| 14 | card holding mechanism |
| 15 | Spreeta ™ SPR transducer, SPR transducer, transducer |
| 16 | sample input reservoir, sample reservoir |
| 17 | test region, test channel |
| 18 | waste reservoir |
| 19 | sample input port, injection port, septum |
| 20 | vacuum output port, vacuum port |
| 21 | metallic test surface chip |
| 22 | drive shaft |
| 23 | functionalization port |
| 24 | optical oil interface, index matching fluid |
| 25 | rack gear, rack |
| 26 | spur gear, pinion |
| 27 | horizontally movable wedge |
| 28 | vertically movable wedge |
| 29 | hydrophobic filter, filter |
| 30 | field deployable surface plasmon resonance based biosensor, biosensor, device |
| 31 | reference region, reference channel |
| 32 | active surface |
| 33 | duct |
| 34 | component fasteners |
| 36 | linear guides |
| 38 | compression springs, springs |
| 40 | insulation |
| 42 | bolts, posts |
| 44 | thermistor wells |
| 46 | thermal device cavity |
| 50 | top cover layer |
| 52 | first adhesive layer |
| 54 | septum spacer layer |
| 56 | second adhesive layer |
| 58 | filter spacer layer |
| 60 | third adhesive layer |
| 62 | reservoir layer |
| 64 | fourth adhesive layer |
| 66 | bottom cover layer |
| 70 | basic temperature control system |
| 72 | set point |
| 74 | first node |
| 76 | differentiator stage |
| 77 | integrator stage |
| 78 | gain stage, proportional stage |
| 80 | second node |
| 82 | copper propagation delay |
| 84 | temperature sensor |
| 86 | pulse-width modulator |
| 88 | H bridge |
| 90 | analog-to-digital converter |
| 92 | digital temperature control system |

DETAILED DESCRIPTION OF THE INVENTION

Figure 2:
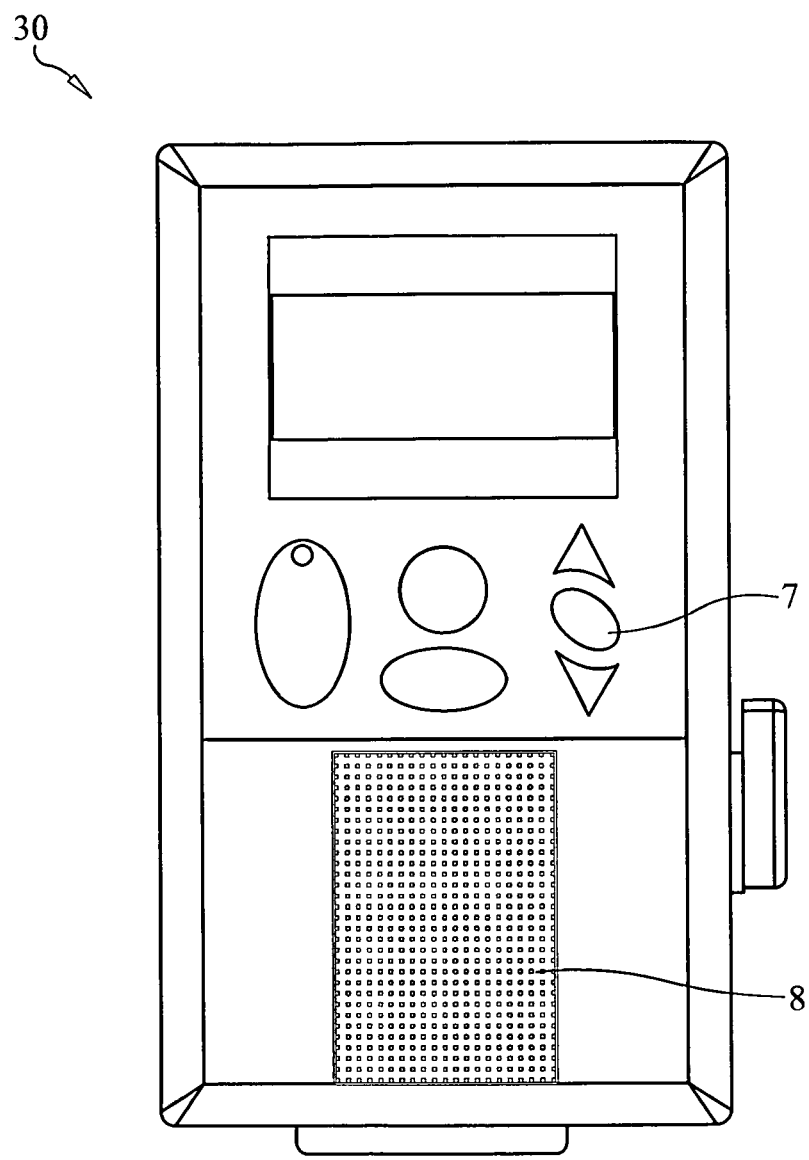
FIG. 2 is a plan (front) view of an illustrative embodiment of the invention.
Figure 3:
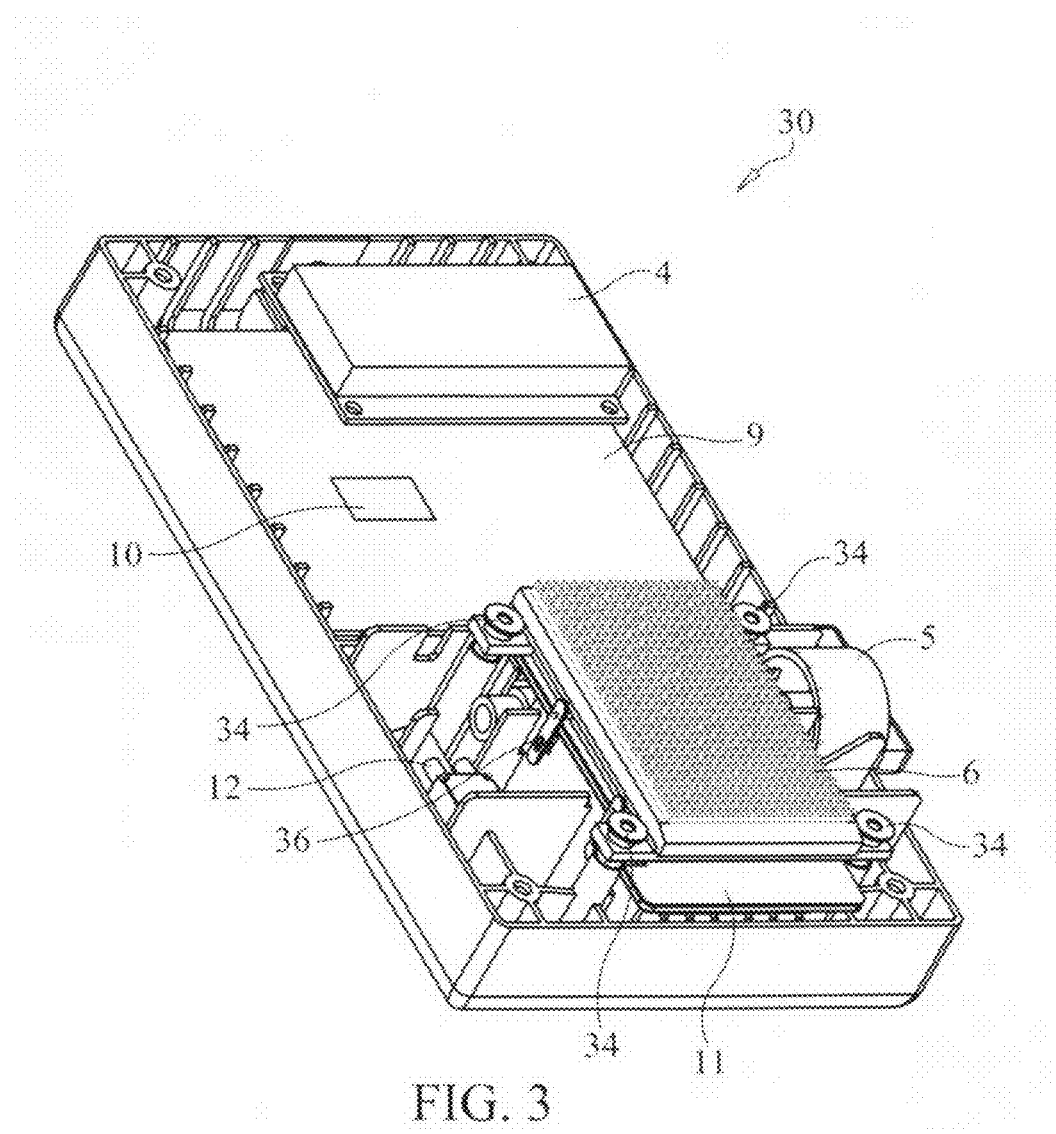
FIG. 3 is perspective view of an illustrative embodiment of the invention with the front cover removed.
Figure 4A:
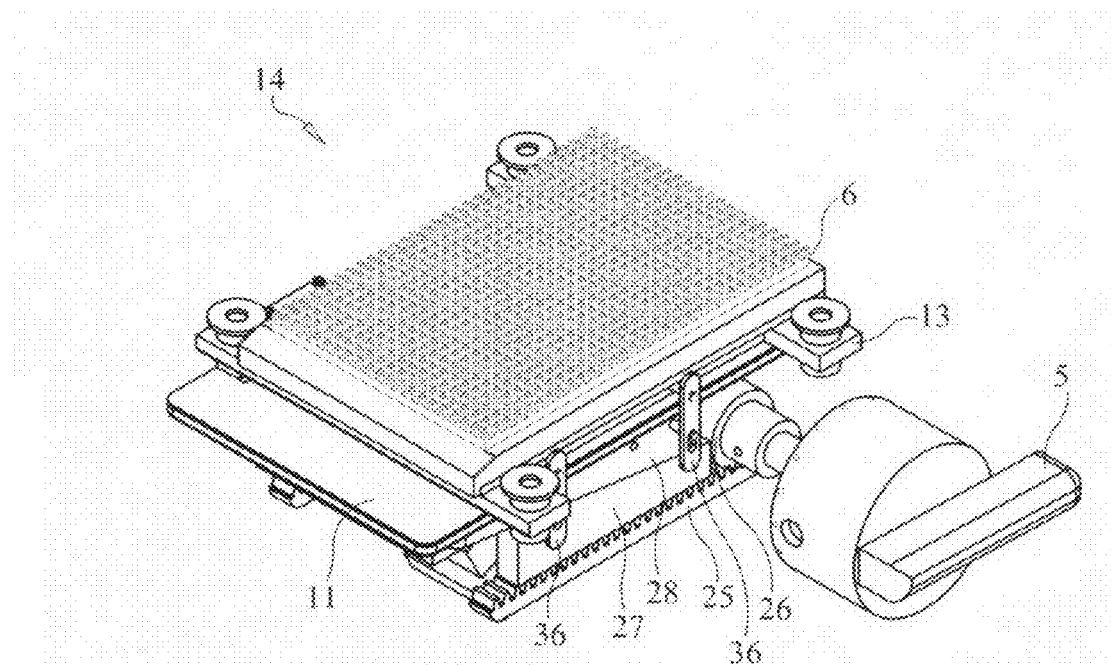
FIG. 4A is a perspective view of the card holding mechanism of an illustrative embodiment of the invention.
Figure 4B:
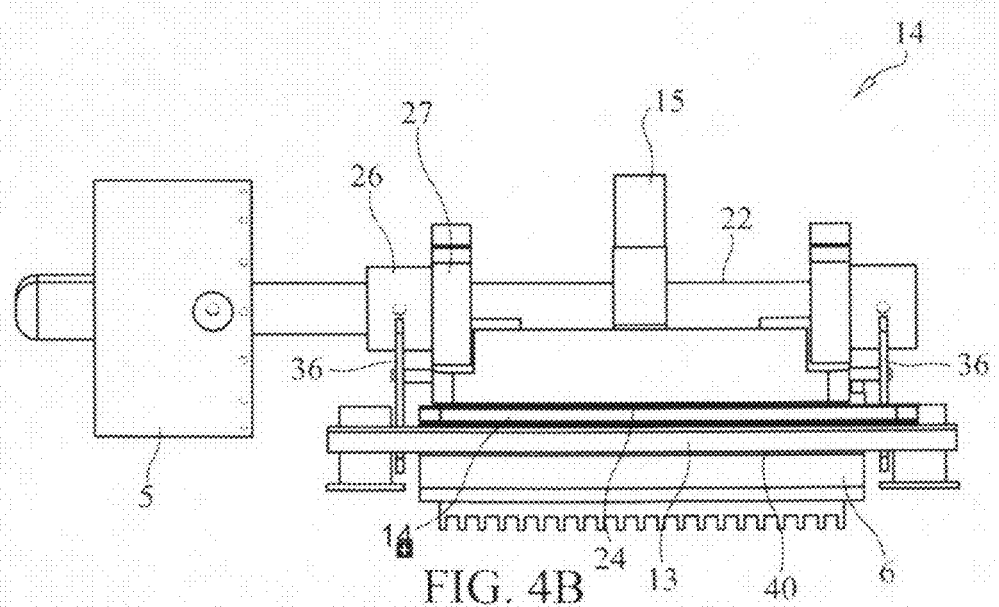
FIG. 4B is an elevation (end) view of the card holding mechanism of an illustrative embodiment of the invention.
Figure 4C:
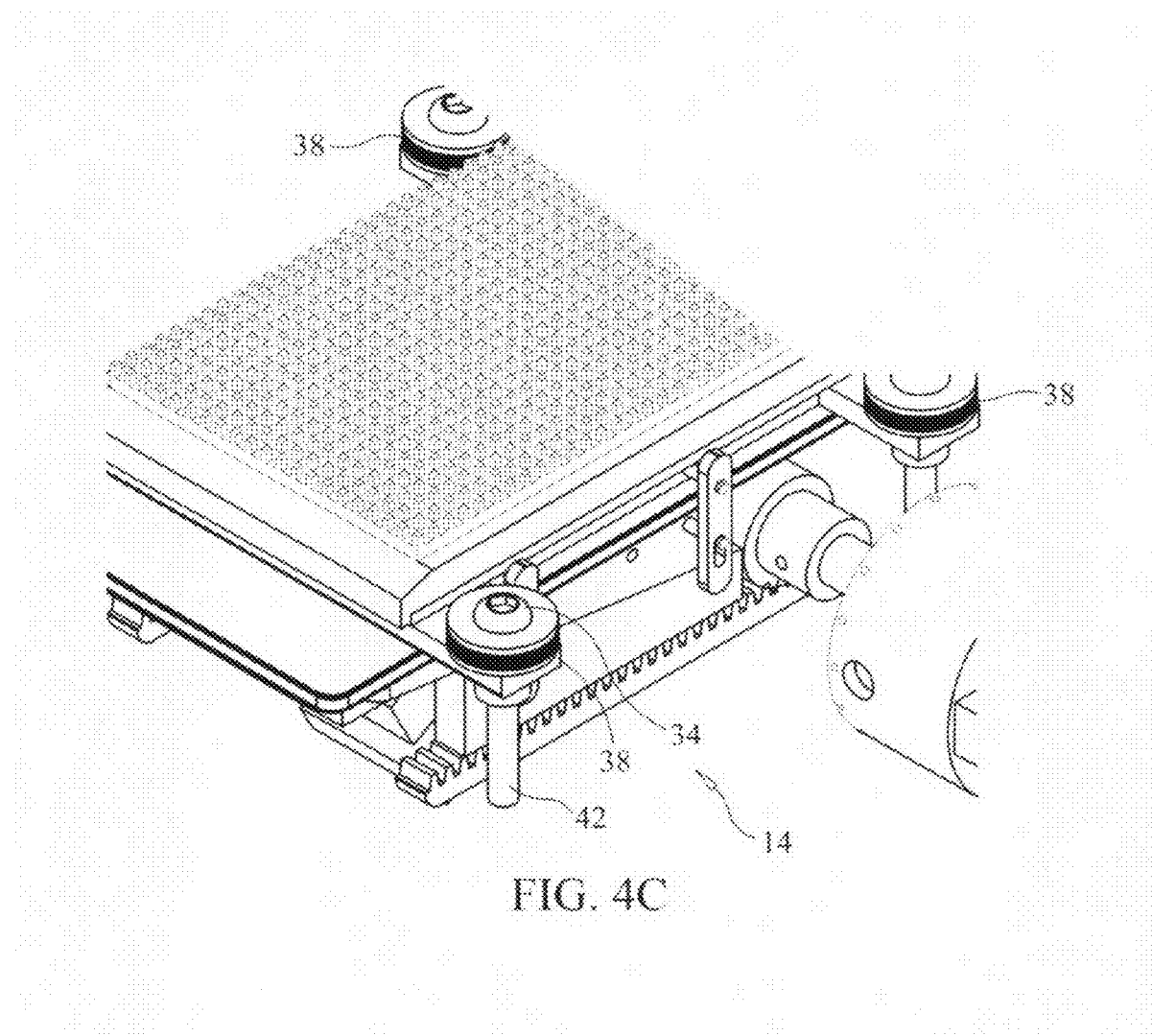
FIG. 4C is another perspective view of the card holding mechanism of an illustrative embodiment of the invention.

Referring to FIGS. 1 and 2, an illustrative embodiment of the invention is presented. In this embodiment, field deployable surface plasmon resonance based biosensor 30 is used to test aqueous samples for analytes of interest. Examples of analytes include proteins, viruses, bacteria, toxins, pathogens, contaminants, chemical compounds, and nucleic acids.

In this embodiment, biosensor 30 is surrounded by a compact housing that comprises top cover 1 and bottom cover 2. Card insertion slot 3 is provided in top cover 1 and display or screen 4, heat sink 6 and control switches 7 protrude through top cover 1. Actuator or knob 5 protrudes from the side of the housing and Peltier assembly 8 protrudes through heat sink 6.

Biosensor 30 is field deployable and may be powered by either alternating current (AC) or direct current (DC) power devices. Biosensor 30 may be used to perform any detection test that is predetermined by a single use, functionalized card 11. In an illustrative embodiment, functionalizing card 11 involves applying an antibody or some other activating agent which is particular to the desired detection test to produce an active surface through a process well known in the art. Functionalization of single use card 11 is preferably accomplished prior to deployment of biosensor 30 to the field. Single use card 11 is placed in device 30 via slot 3.

Referring to FIGS. 3, 4A, 4B, and 4C, after card 11 is inserted in horizontal card insertion slot 3, the card is pressed down against SPR transducer 15 by turning knob 5 of card holding mechanism 14. In this embodiment, turning knob 5 rotates spur gear 26 which interfaces with rack gear 25 causing linear motion of rack gear 25. Rack gear 25 is preferably attached to a wedged shaped component (horizontally movable wedge 27) with standard screws. Horizontally movable wedge 27 has an upper surface disposed at a first angle relative to horizontal (as that term is designed above) that is in contact with another wedge (vertically movable wedge 28) that has a lower surface that has a second angle that is complementary to the first angle of the upper surface of horizontally movable wedge 27. The first angle and the second angle are complementary in that they sum to ninety degrees.

In this embodiment, vertically movable wedge 28 is vertically movably attached to heat storage component 13. Heat storage component 13 is preferably made of copper or another substance with a similar thermal capacitance and is fixed to bottom cover 2 by means of component fasteners 34 (e.g., washers) and bolts 42. Linear guides 36 are fixed to heat storage component 13 that have slots into which posts on vertically movable wedge 28 are vertically movable, which restricts the motion of vertically movable wedge 28 to vertical (as that term is defined above).

In this embodiment, compression springs 38 are disposed concentric to bolts 42 beneath component fasteners 34 and exert a downward force on heat storage component 13. By turning knob 5 clockwise, springs 38 are compressed by the upward motion of heat storage component 13, allowing the insertion or removal of card 11. Turning knob 5 counterclockwise allows springs 38 to exert a downward force on heat storage component 13, causing card 11 to be pressed against SPR transducer 15. Illustrative embodiments of SPR transducer 15 are disclosed in U.S. Pat. Nos. 5,912,456 (see especially FIG. 2) and 6,870,627 (see especially FIG. 3); the disclosures of which patents are incorporated by reference as if fully set forth herein. In the embodiments disclosed herein, there is no metallic layer or coating on the light transmissive window of the SPR transducer. Rather, the metallic layer or coating is provided on metallic surface chip 21.

This arrangement allows for a constant (from one card insertion to the next) force as supplied by the springs 38 and not from unregulated/uncontrolled force supplied by the operator (by turning knob 5). Springs 38 are guided by posts 42 that are arranged vertically in respect to card 11. Springs 38 exert a force on heat storage component 13 which transfers the force to card 11 and the associated interface between card 11 and SPR transducer 15 which is preferably index matching fluid 24.

In an illustrative embodiment, operation of device 30 is accomplished by manipulation of switches 7 which are mounted on top cover 1. Responses and user feedback are displayed on screen 4. Many levels of operation are possible depending on the desired result. In a simple operating mode, a positive or negative indication of detection of an analyte is displayed. In a more advanced operating mode, SPR curves and detection level are displayed. In a preferred embodiment, a positive or negative test result for the analyte targeted by single use card 11 and analyte concentration are displayed on screen 4 along with instrument status and brief instructional prompts.

Because the SPR technique is sensitive to shifts in temperature, a temperature control method is employed. In an illustrative embodiment, a Peltier assembly 8 is utilized to heat and cool heat storage component or thermal mass 13. In an illustrative embodiment, Peltier assembly 8 maintains heat storage component 13 at the desired test temperature, e.g., between 20 and 30 degrees Celsius (° C.), controlled to within desired limits. In an illustrative embodiment, from test to test the temperature is held within +/−5° C. and within a test the temperature is held to within +/−0.1° C.

Heat storage component 13 is used to precondition and maintain card 11 and the sample it contains at the desired test temperature. In an alternative embodiment, final and fine temperature control is accomplished by resistively heating the metallic test surface chip 21 to the final required test temperature.

Unlike the device disclosed in U.S. Patent Application No. 2010/0284012, in which a card made of silicone is used (which was selected for its insulative properties), a more preferred embodiment disclosed herein uses a card 11 made of polyethylene terephthalate (PET), acrylic and a pressure sensitive adhesive, which were selected because of their thermal conductive natures. As noted above, the amount of material in card 11 is minimized for heat transfer reasons and the sample fluid layer is thin for like reasons. This approach allows the achievement of very fine temperature control that is capable of maintaining the test area at a precise setting.

Figure 5A:
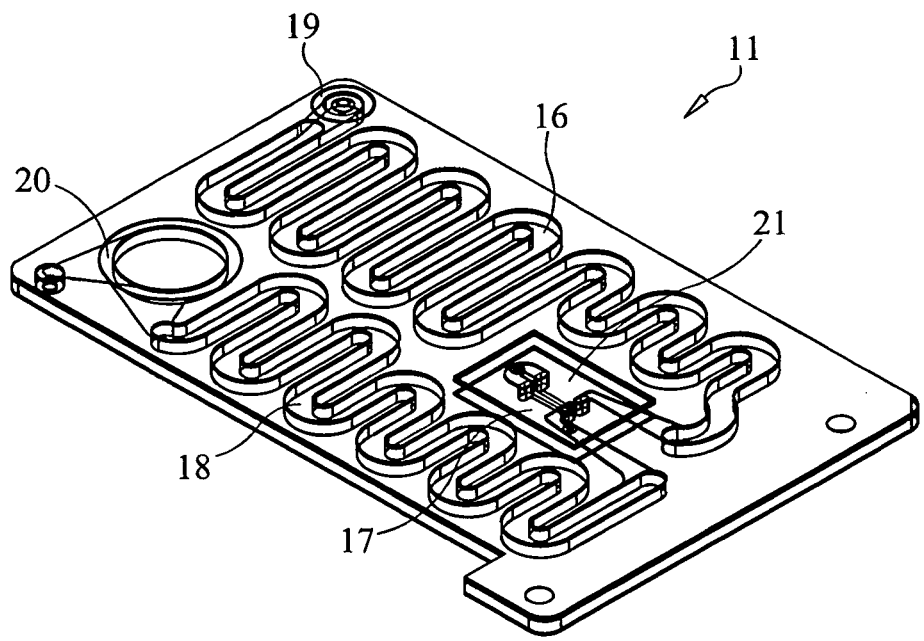
FIG. 5A is a perspective view of the card of an illustrative embodiment of the invention.
Figure 5B:
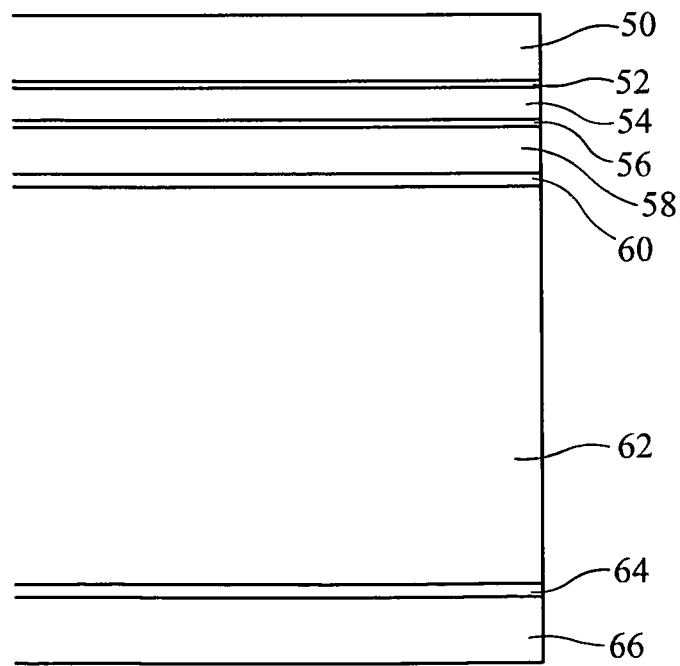
FIG. 5B is an elevation (end) view of the card of an illustrative embodiment of the invention.
Figure 5C:
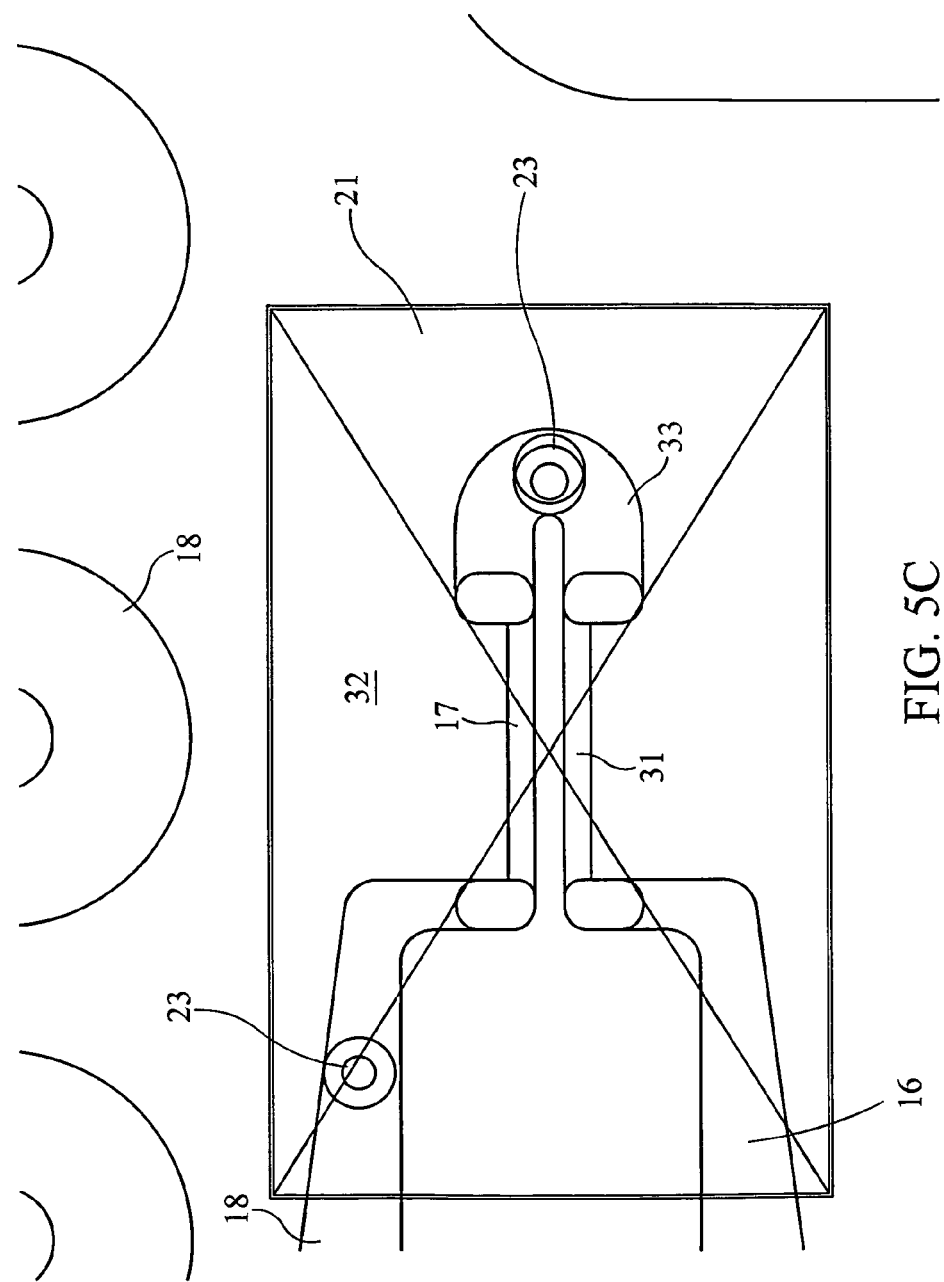
FIG. 5C is a plan drawing of the active surface portions of the card of an illustrative embodiment of the invention.

Referring to FIGS. 5A, 5B and 5C, views of an illustrative embodiment of card 11 comprising a microfluidic system are presented. Testing of a sample involves introducing about 0.5 milliliters (ML) of sample into card 11 by injecting it through septum 19 with a syringe, pipette or similar device. Septum 19 both allows insertion of the sample fluid and retains the fluid. During a test, sample fluid is moved from sample reservoir 16 across a functionalized (activated) surface on metallic test surface chip 21 through test channel 17 on the single use card 11 by means of pump 12. Pump 12 may either be attached to injection port 19, if movement of a sample fluid is to be driven by pressure, or to vacuum port 20 if the sample fluid is to be pulled across by vacuum. A preferred embodiment employs a vacuum pump 12 that is optimized to generate the desired flow rate of 20 to 40 microliters per minute (μL/min). The applicants discovered that this rate was rapid enough to enable fluidic movement through channels 16, 17 and 18, while slow enough to avoid undesirable outcomes such as sheer or bubble generation (which would incapacitate sample movement).

In either case, the sample is transported from sample reservoir 16, through test channel 17 over the functionalized test area and into waste reservoir 18. Test channel 17 is about 0.002 inches in depth by about 0.020 inches in width. Each channel/reservoir 16 and 18 is preferably optimized at the following dimensions: 7 millimeters (mm) long, by 0.55 mm wide by, 0.05 mm thick in a serpentine path across card 11. At the completion of a test, the sample is maintained in waste reservoir 18 for containment of a potentially hazardous substance or for further testing in an appropriate facility. The sample may be removed from card 11 through septum 19 by either applying pressure to drive it out by using a vacuum to pull it out. Control active surface 32 is a portion of metallic test surface chip 21 that is not exposed to the sample. The test active surface is located at the bottom of a portion of test channel 17 and is exposed to the sample.

In an illustrative embodiment, filter 29 is built into card 11 and is in fluid communication with waste reservoir 18 and vacuum port 20. Filter 29 is preferably fabricated from a cellulose material that has been treated to render it hydrophobic (e.g., Whatman 1PS Phase Separator manufactured by Whatman Inc. of Piscataway, N.J.). Filter 20 retains fluid in card 11 but allows air to pass through vacuum port 20.

Referring to FIG. 5B, an elevation cross-sectional view at the edge of an illustrative embodiment of card 11 is presented. In this embodiment, the layers of card 11 are preferably fabricating by cutting each layer from a sheet of material using a carbon dioxide laser and then stacked. The layers are adhered together using a pressure sensitive adhesive (PSA) (e.g., 3M8211, silicone PSA manufactured by 3M Corporation, Minnesota).

In this embodiment, top cover layer 50 is preferably fabricated from PET and forms the top of the channels 16 and 18. Top cover layer 50 holds septum 19 and filter 29 in card 11. First adhesive layer 52 joins top cover layer 50 and septum spacer layer 54. Septum spacer layer 54 contains septum 19 and spaces the adjacent layers apart and is preferably fabricated from PET. Second adhesive layer 56 joins septum spacer layer 54 and filter spacer layer 58. Filter spacer layer 58 contains filter 29 and spaces the adjacent layers apart and is preferably fabricated from PET. Third adhesive layer 60 joins filter space layer 58 and reservoir layer 62. Channels 16 and 18 are formed in reservoir layer 62 which is preferably fabricated from acrylic. Fourth adhesive layer 64 joins reservoir layer 62, metallic test surface chip 21, and bottom cover layer 66. The top surfaces of metallic test surface chip 21 and bottom cover layer 66 are coplanar. Bottom cover layer 66 forms the top of channels 16 and 18 and captures filter 29. Bottom cover layer 66 is preferably fabricated from PET.

Card 11 is preferably configured to hold enough sample fluid to complete an assay (approximately 0.5 mL). Fluid flow across card 11 preferably transfers 0.5 mL from sample reservoir 16 to waste reservoir 18 in 20 minutes. In an illustrative embodiment, sample fluid flows through two channels connected in series: the first channel is a reference channel to be used for comparison, and the second channel is the SPR channel. After the fluid has passed through the two channels, it is held in waste reservoir 18 (approximately 0.5 mL). Past waste reservoir 18, hydrophobic filter 29 is used to retain the sample in card 11. Channel design is a balance between cost and pressure drop due to flow restriction. Capillary forces are taken into account as well as viscous friction. In a preferred embodiment, the flow restriction (pressure drop) is limited to that which could be achieved by a small vacuum pump. Vacuum is preferred for its inherent safety benefits (e.g., with leaks occurring into card 11 rather than out from card 11). The fluid sample is preferably spread out over as much test surface as possible. In this embodiment, the channels are required to be small in cross-sectional area, which dictates that they be limited to an adhesive layer (removed material in the adhesive layer). Card layers of card 11 are preferably held together with a contact adhesive (substrate free glue). The benefits of a single use card design include: no cleaning is required between assays; the transducer never comes in contact with the sample; each card is pre-functionalized (ready to use); each card is contamination free; each card retains the sample (for further testing back in a laboratory); assay turnaround is rapid; changing from one assay to another is facilitated by using another pre-functionalized card; major time and cost savings are achieved; much greater portability is achieved; and less knowledge is required to operate device 30.

In an illustrative embodiment, metallic test surface chip 21 is fabricated from glass with a gold coating deposited by physical vapor deposition. The area of metallic test surface chip 21 is sufficient to cover the light transmissive window in SPR transducer 15, which light transmissive window does not have a gold layer or which has had its gold layer removed. Preferred specifications for metallic test surface chip 21 are presented in Table 1.

TABLE 1

Metallic Test Surface Chip Specifications

| Item | Parameter |
| --- | --- |
| Material | Glass |
| Refractive index | 1.590 (+/−0.01) @ 900 nm wavelength |
| Thickness | 0.31 mm (+/−0.02 mm) |
| Flatness | 0.001 mm |
| Parallel surfaces | <1/3° taper in any direction |
| Width | 12.5 mm (+/−0.0635 mm) |
| Length | 18.86 mm (+/−0.0635 mm) |
| Coating | Au (gold) |
| Quality | 99.99% pure |
| Thickness | 50 nm (+/−2.5 nm) |
| Bond layer | Titanium or Chromium |
| Bond layer thickness | <10 Å |

In an illustrative embodiment, the channels 16, 17, 18, 31 are created by cutting a path into the adhesive to form the sides (only 0.002 thick) and by using the adjoining layers to form the tops and bottoms of the channels. In this embodiment, gold coated metallic test surface chip 21 is much larger than the channels and covers a larger than required area. It is not economically viable to gold coat only the channel areas. It is also preferable that the test channels or any fluid pathway (duct) not cross over a joint between two material layers or components. For this reason, gold coated chip 21 is relatively large.

Referring to FIG. 5C, in an illustrative embodiment, active surface 32 of sensor card 11 is disposed on metallic test surface chip 21. Two regions bear different surface functionality to serve as monitored regions from which SPR dips are gathered; this includes reference region 31 and sample region 17. In this embodiment, reference region 31 is covered with a monolayer that prevents non-specific binding, and bears no other functionalization or specificity to a particular analyte of interest. Its role is to characterize the sample solution to provide a relative dip position to which the sample channel is compared. Sample region 17 is also functionalized with a monolayer to prevent non-specific binding, as well as tethers to which biomolecules or chemical receptors are attached, providing functional specificity of the surface to a particular analyte of interest.

In that biomolecules are utilized in the detection and quantification of analytes, a preservative is preferably used to maintain their functional state. This preservative is injected into the card at functionalization port 23 and is drawn via a vacuum to the other functionalization port 23. Following this preservation step, functionalization ports 23 are sealed prior to shipment of card 11. This liquid-based preservative may be dried in situ or maintained in a fluidic state on card 11 until use. An example of such a preservative is ProClin 300 manufactured by Rohm and Haas of Philadelphia, Pa.

In an illustrative operating sequence, a test sample is drawn by vacuum pump 12 from sample reservoir 16 and then into the reference channel 31. As no functional molecules are present on the active surface of reference channel 31, this surface examines the bulk refractive index of the test sample. The test sample is then drawn through duct 33 which links reference channel 31 to test channel 17. Test channel 17, due to its functional specificity to a desired analyte, binds any such analyte in the test sample, effectively changing the angle at which SPR occurs. The change in SPR angle of test channel 17 relative to the change in SPR angle of reference channel 31 over time is therefore directly proportional to the quantity of bound analyte, providing the means for the instrument to detect and quantify the target analyte.

Controller 9 is preferably used to control sample temperature, sample movement, sample data acquisition, sample data analysis and user feedback. In an illustrative embodiment, controller 9 is a microprocessor that has the required speed to achieve all control functions. In a preferred embodiment, three Micro Controller PIC processors are used (one for the Spreeta transducer, one for thermal control, and one for the human machine interface). The processors' speed allows hundreds of thousands of data points to be taken and analyzed per second. In an alternative embodiment, a single, faster processor is used to accomplish all three control functions.

Figure 6A:
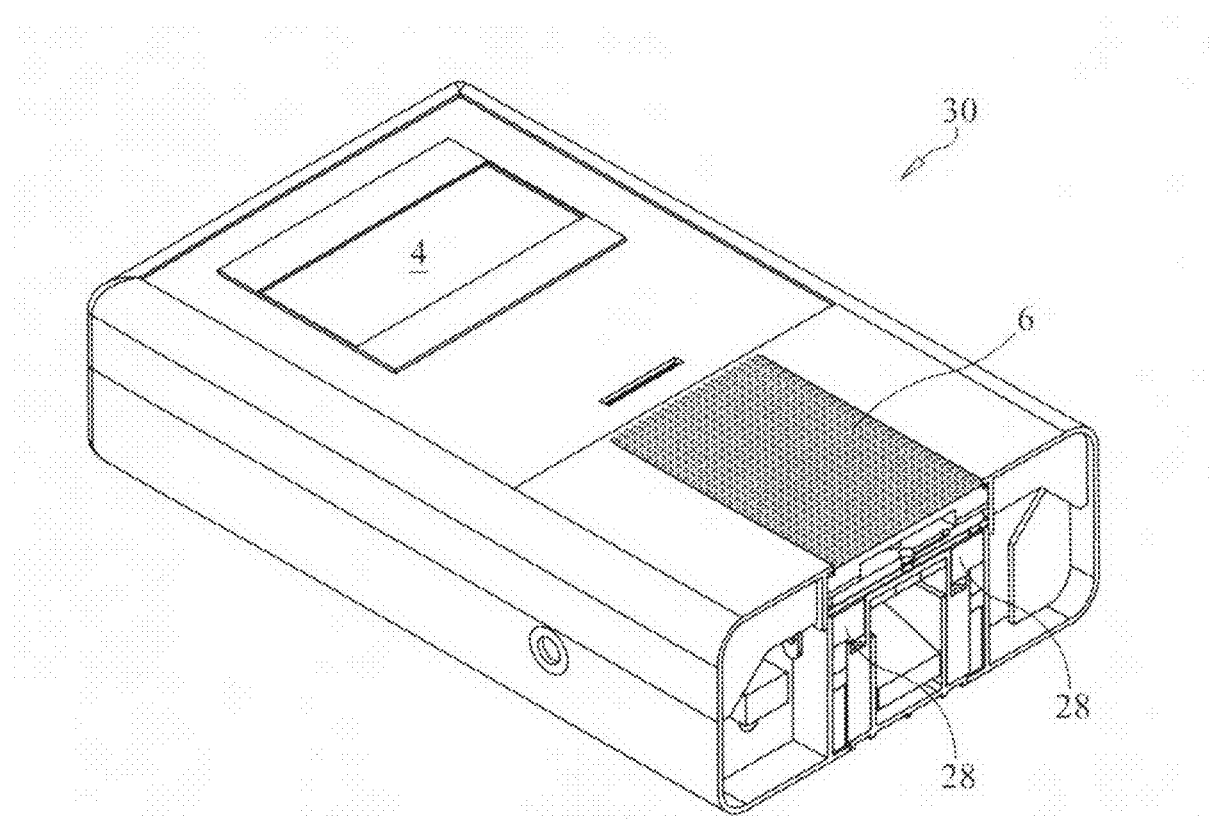
FIG. 6A is a cross sectional view of an illustrative embodiment of the biosensor showing the card holding mechanism in place.
Figure 6B:
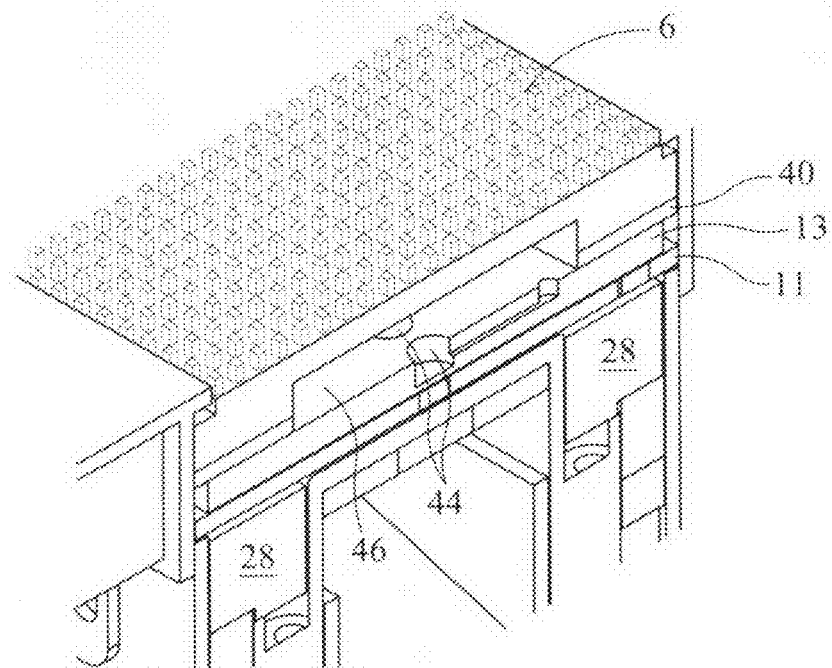
FIG. 6B is a zoomed in version of the cross sectional view of FIG. 6A.

Referring to FIGS. 6A and 6B, cross sectional views of an illustrative embodiment of biosensor 30 are presented with card 11 inserted. In this view, card 11 is held in place between thermal mass 13 and vertically movable wedges 28. Thermal reservoir 13 is provided with thermister wells 44 in which thermistors 84 (not shown in FIGS. 6A and 6B) are installed. Thermistors 84 produce signals that are indicative of the temperature of thermal reservoir 13, and, hence, of the temperature of adjacent card 11. In this view, Peltier assembly 8 is not shown in thermal device cavity 46 for clarity. In a preferred embodiment, Peltier assembly 8 is Peltier (TEC) Module 19811-9L31-02CN1 manufactured by Custom Thermoelectric of Bishopville, Md. which is controlled by MAX1978ETM Integrated Temperature Controllers manufactured by Maxim Integrated Products, Inc. of Sunnyvale, Calif.

Figure 7A:
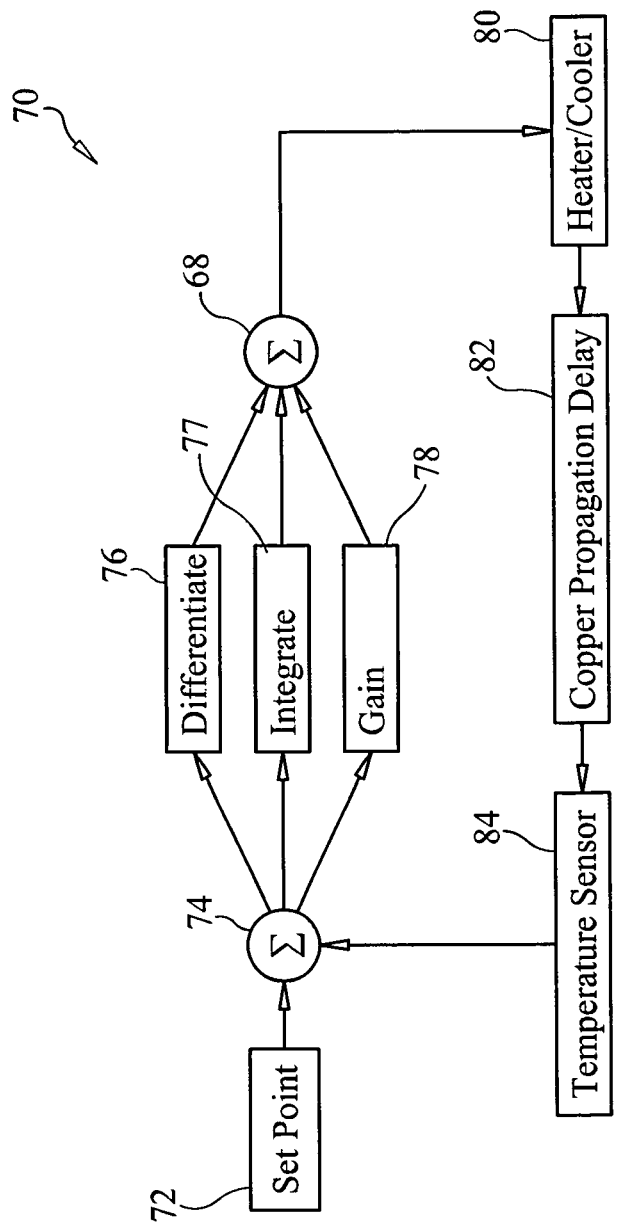
FIG. 7A is schematic block diagram illustrating a basic temperature control system in accordance with an illustrative embodiment of the invention.
Figure 7B:
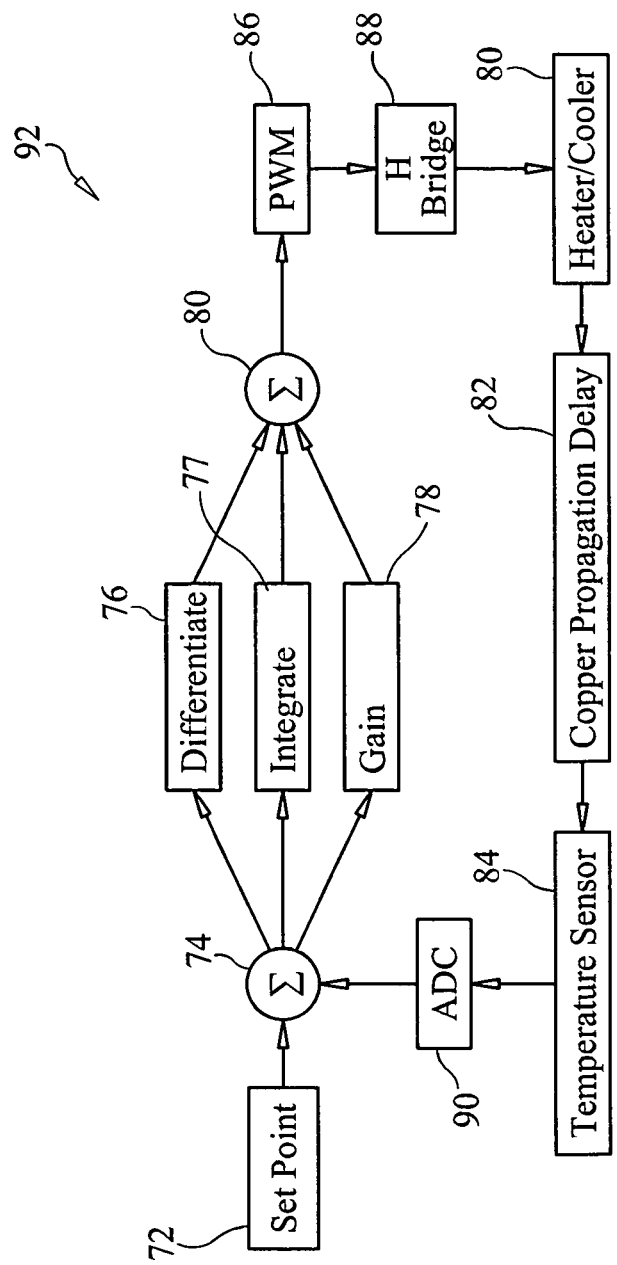
FIG. 7B is schematic block diagram illustrating a digital temperature control system in accordance with an illustrative embodiment of the invention.

Referring to FIGS. 7A and 7B, schematic block diagrams illustrating a basic temperature control system in accordance with an illustrative embodiment of the invention are presented. The basic temperature control system is presented in FIG. 7A. In this embodiment, basic temperature control system 70 comprises set point 72, first node 74, differentiator stage 76, integrator stage 77, gain stage 78, second node 80, heater/cooler 8, copper propagation delay 82, and temperature sensor 84. To implement this system as a digital control system, certain latitude is taken with basic concepts that introduce quantification effects. Digital temperature control system 92 comprises set point 72, node 74, differentiator stage 76, integrator stage 77, gain stage 78, node 80, heater/cooler 8, copper propagation delay 82, temperature sensor 84, pulse-width modulator (PWM) 86, H bridge 88, and analog-to-digital converter (ADC) 90.

Integrator stage 76, differentiator stage 77 and gain stage 78 are preferably implemented as periodic updates. In a pure analog PID loop embodiment, these elements would run continuously within the bandwidth of the circuitry. The scaling (gain) factor for each block would be set with component values (capacitors for the differentiator stage and integrator stage) and resistor ratios for the gain (proportional) stage. When implemented digitally, the "gain" of the integrator and differentiator are set by the frequency of updates and the proportional stage gain is set by a scaling factor.

In this embodiment, the performance of heater/cooler 8 is very nonlinear. Heater/cooler 8 creates a temperature differential between two surfaces. The temperature of active surface 32 of metallic test surface chip 21 depends on the temperature of thermal mass 13, as well as the current, or in this case, the duty cycle of H-bridge 88. Not shown is a delay in heater/cooler 8. For simulation purposes, it is assumed that the response of heater/cooler 8 is significantly faster than the propagation of temperature through thermal mass 13. The goal is to create a uniform temperature in thermal mass 13. To accomplish this, provision of a temperature sensor 84 on the card side of heat sink 6 is preferred. In an alternative embodiment, multiple temperature sensors 84 are used. In another alternative embodiment, multiple heater/cooler 8 elements operating approximately in parallel are used.

In response to a step input change in set point 72 or a reading from thermistor 84, each of the response stages has a different response. Proportional stage 78 creates a step in the width of the signal from PWM 86 that is proportional to the error voltage. Proportional stage 78 cannot drive the error between set point 72 and measured temperature to zero and the PWM width is proportional to the error. If the error is driven to zero, the PWM width contribution from this stage is zero.

The purpose of integration stage 77 is to slowly drive the error to zero. This effect compensates for the inability of proportional stage 78 to do so. Changes in the integration contribution must be slow compared to the delay through the feedback system (that is, compared to copper propagation delay 82) to prevent overshoots. Integrator stage 77 has infinite gain at direct current (DC). This drives all poles toward the right hand pole, and a tendency to oscillate wildly can result.

The purpose of differentiator stage 76 is to introduce a rapid one-time response to a change in the error signal. A rising error signal causes a pulse in heater control voltage that creates a quick response to a sharp change in the set point or measured temperature.

The requirement for precise temperature control makes the integration stage part of the control loop important if the error value is to be driven to zero. The proportional stage 78 is needed to produce a faster response.

In an illustrative embodiment, set point 72 is constant. After biosensor 30 is turned on, thermal mass 13 is brought up to temperature and remains there. Thus, system 92 does not have to track set point.

It can be appreciated that other components are capable of achieving similar results and the descriptions given herein are to be taken as an example of an embodiment.

Working Example

Temperature drift studies on an embodiment of the invention disclosed herein showed temperature stability over a sixty minute period within 0.15 degrees C. This has a profound impact on improved sensitivity of the device An experiment to determine temperature drift was performed. The instrument was allowed to equilibrate (rest) in the test location for 30 minutes prior to testing. Next, a test card was loaded with a filtered, deionized water sample. The loaded test card 11 was placed into the instrument as per standard protocol (pressed fully into biosensor 30 and knob 5 was rotated to the test or card holding position). Then biosensor 30 was supplied with power and turned on. Upon startup, biosensor 30 established a thermal set point three degrees above ambient temperature and began heating to that set point.

Next, vacuum pump 12 was started and run until a signal was achieved on both channels (reference or control and sample or test), then stopped. Data were taken for 35 minutes under no-flow conditions to determine thermal stability without flow. This process continued while vacuum pump 12 was again started for a period of 20 minutes under flow conditions to determine thermal stability with flow. Finally, flow, data acquisition, and thermal management were all terminated at the end of the test period. Data were taken from the biosensor 30 which were used to produce the plots shown in FIGS. 8A and 8B. Dip position is an indicator of the refractive index of the test solution, and therefore is used to indicate the presence of any bonded analyte.

RU is the preferred unit of measure for biosensor 30. Thermal drift may be measured in RU, as it directly relates to the measurements already taken by the instrument. A temperature change of 1 degree Celsius has an impact of approximately 100 RU at temperatures near room temperature in which the instrument was operated. RU are called 'refractive units' and constitute one millionth of one RIU (refractive index unit, also known as RI when absolute). RI are units more familiar to the layperson. These units are measures of the absolute index of refraction: where the RI of air is 1.0, water is 1.33, glass around 1.52, etc. As the instrument measures changes in refractive index as the means of its sensitivity, it makes sense to express the output in terms of such changes.

Figure 8B:
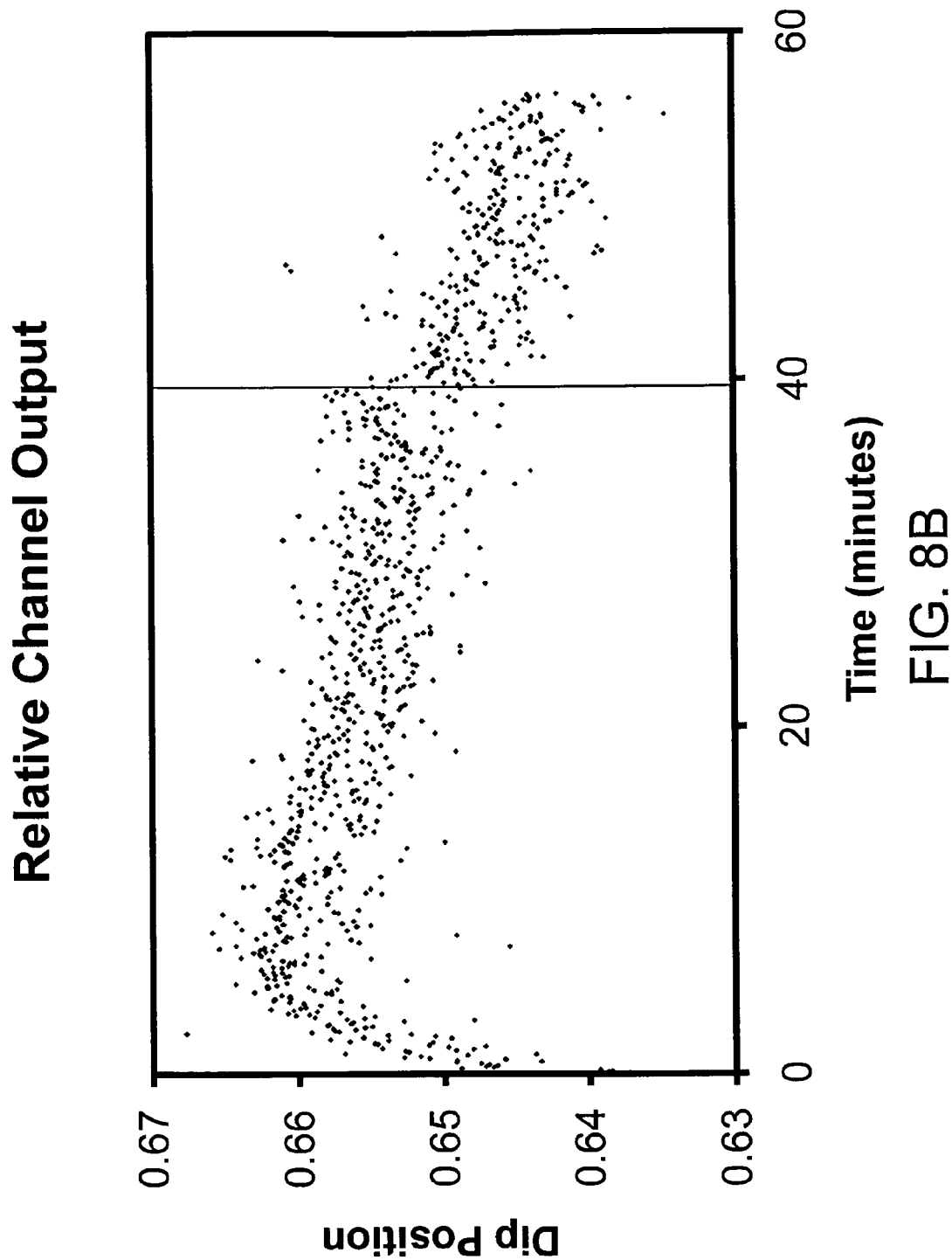
FIG. 8B is a detailed plot of the results displayed in FIG. 8A to scale permitting analysis of outliers and average results.

The plots presented in FIGS. 8A and 8B reveal the following: Thermal drift over the course of a sixty minute period was very small (36 RU), meaning that the total drift over the sample period of 20 minutes was 12 RU and 1.5 RU respectively; putting the embodiment on par with laboratory size biosensors that retail for over $100,000. In addition, the embodiment presents relative stability of the signal, translating to stability and reliability of the measurement.

Although some embodiments are shown to include certain features or steps, the applicants specifically contemplate that any feature or step disclosed herein may be used together or in combination with any other feature or step on any embodiment of the invention. It is also contemplated that any feature or step may be specifically excluded from any embodiment of the invention.

What is claimed is:

1. A sensor comprising:
   a housing having a card slot, a heat sink opening, a knob opening and a display opening;
   an integrated surface plasmon resonance transducer that is disposed within said housing;
   a functionalized card disposed in said card slot, said functionalized card comprising a body having an upper wall having an upper outer surface and a lower wall having lower outer surface and a microfluidic channel having a sample input port that is provided with a septum, a sample input reservoir that is in fluid communication with said sample input port, a test channel and a reference channel that are in fluid communication with said sample input reservoir, a waste reservoir that is in fluid communication with said test channel and said reference channel, a hydrophobic filter that is in fluid communication with said waste reservoir, a vacuum output port that is in fluid communication with said hydrophobic filter and a chip having a metallic test surface that forms an interior wall of said test channel and an inner wall of said reference channel for producing said reflection;
   an index matching fluid disposed between said integrated surface plasmon resonance transducer and said lower outer surface and adjacent to said metallic test surface;
   a card holding mechanism for positioning said functionalized card against said integrated surface plasmon resonance transducer, said card holding mechanism comprising a spring that is operative to urge said functionalized card toward said integrated surface plasmon resonance transducer and a card releasing mechanism comprising a knob that is disposed in said knob opening, a drive shaft that is attached to said knob, a spur gear that is attached to said drive shaft, a rack gear for engaging with said spur gear, a horizontally movable wedge for engaging with said rack gear and a vertically movable wedge for engaging with said horizontally movable wedge and with said card, said card releasing mechanism being operative to reverse the motion urged by said spring when said knob is rotated;
   a heat storage component that is disposed adjacent to said functionalized card and is in contact with said upper outer surface, said heat storage component having a thermistor well, an insulation layer that is disposed adjacent to said heat storage component, a heat sink that is disposed in said heat sink opening, said heat sink having a cavity that is disposed adjacent to said insulation layer, a heating and cooling device that is disposed adjacent to said heat storage component and in said cavity, and a thermistor that is disposed in said thermistor well;
   a vacuum pump that is in fluid communication with said vacuum output port that is operative to move a sample that has been injected into said sample input port through said microfluidic channel, said vacuum pump being disposed in said housing;
   a power source that is disposed within said housing;
   a plurality of control switches that are mounted on said housing;
   a control circuit interface board that is disposed within said housing;
   a computer/controller that is disposed within said housing, said computer/controller being operative to receive signals from said thermistor and control the temperature of said heat storage component and to process signals from said integrated surface plasmon resonance transducer and to produce an output; and
   a display that is mounted in said display opening and that is operative to receive and display said output.

2. The sensor of claim 1 wherein said heating and cooling device comprises:
   a Peltier assembly.

3. The sensor of claim 1 wherein said functionalized card further comprises:
   a top cover layer that provides a top for said sample input reservoir and said waste reservoir and that holds said septum and said filter in said functionalized card;
   a septum spacer layer that contains said septum;
   a first adhesive layer that joins said top cover layer and said septum spacer layer;
   a filter spacer layer that contains said filter;
   a second adhesive layer that joins said septum spacer layer and said filter spacer layer;
   a reservoir layer in which sample input reservoir and said waste reservoir are formed;
   a third adhesive layer that joins said filter spacer layer and said reservoir layer;
   a bottom cover layer that provides a bottom for said sample input reservoir and said waste reservoir; and
   a fourth adhesive layer that joins said reservoir layer and said bottom cover layer.

4. The sensor of claim 1 wherein said interior wall is functionalized and said inner wall is not.

5. A surface plasmon resonance analytical kit comprising:
   a housing comprising a card slot, a heat sink opening and a display;
   means for measuring a surface plasmon resonance comprising an integrated surface plasmon resonance transducer that produces a signal;
   a functionalized card comprising a microfluidic active surface, a reference channel active surface, a waste reservoir and a hydrophobic filter, said functionalized card being adapted to receive a sample in a test channel; means for holding said functionalized card in optical communication with said integrated surface plasmon resonance transducer, said means for holding comprising elastic members that exert forces that urge said functionalized card toward said integral surface plasmon resonance transducer; means for releasing said functionalized card comprising a user accessible knob, a drive shaft that is attached to said know, a spur gear, a horizontally movable wedge, a vertically movable wedge that interacts with said horizontally movable wedge, a rack that is attached to said horizontally movable wedge, and a pinion that interacts with said rack and that is attached to said user accessible knob that are operative to overcome said forces and allow said functionalized card to move away from said integral surface plasmon transducer; and means for processing said signal to produce an indication of whether said sample contains an analyte of interest;

a chip having a metallic test surface;

an index mating fluid;

a heat storage component that is disposed adjacent to the functionalized card comprising a well, an insulation layer, a heating and cooling device, a thermistor, a vacuum pump, a power source, a plurality of control switches, a control circuit interface and a computer/controller.

6. A field deployable surface plasmon resonance based biosensor comprising: a functionalized card comprising a microfluidic system that delivers a sample to functionalized test surface chip in a test channel, in a reference channel and a waste reservoir; a hydrophobic filter, a chip having a metallic surface, an index matching fluid, a card holding mechanism that comprises springs that hold said functionalized card in a card holding position during a test and a user accessible knob, a drive shaft that is attached to said know, a spur gear that is attached to the drive shaft, a pinion, a rack for engaging the spur gear and wedges that are operative by a user to compress said springs when said card holding mechanism is in a card releasing position before and after said test, said wedges comprising a horizontally movable wedge that has an upper surface disposed at a first angle and a vertically movable wedge that has a lower surface that has a second angle that is complementary to said fast angle; a thermal control system that is operative to control the temperature of said functionalized card indirectly by controlling the temperature of a thermal mass that is disposed adjacent to said functionalized card when the card holding mechanism is in the card holding position; a heat storage well, an insulation layer, a heat sink, a thermistor, a vacuum pump, an integrated surface plasmon resonance transducer that is operative be in optical communications with said activated funtionalized test surface chip and is operative to characterize reflections from said functionalized test surface chip and produce output signals; a processor that is operative to process said output signals; and a user interface comprising switches and a display that is operative to accept input from a user and to present biosensor results to said user.

7. The field deployable surface plasmon resonance based biosensor of claim 6 wherein said thermal control system comprises a Peltier assembly.

8. A sensor comprising: a housing; an integrated surface plasmon resonance transducer that is disposed in said housing, said integrated surface plasmon resonance transducer producing a signal; a functionalized card comprising a test channel, a reference channel, and waste reservoir, a hydrophobic filter, a chip having a metallic test surface; an index matching fluid that is disposed between said integrated surface plasmon resonance transducer and said functionalized card; a card holding mechanism comprising a spring that urges said functionalized card against said integrated surface plasmon resonance transducer; a card releasing mechanism comprising a knob, a drive shaft attached to said knob, a spur gear attached to said drive shaft, a rack gear for engaging said spur gear, a horizontally movable wedge for engaging said rack gear, and a vertically movable wedge for engaging said horizontally movable wedge; a temperature control component comprising a well, an insulation layer, a heat sink, a heating/cooling device, and a thermistor; a vacuum pump for moving a sample through said test channel and said reference channel; a power source for powering the sensor; a plurality of control switches that are mounted on said housing; a control circuit interface for controlling the sensor; a computer/controller for interpreting said signal to produce an output; and a display for displaying said output.

9. The sensor of claim 8 wherein said output is a concentration of an analyte in said sample.

10. The system of claim 8 wherein said vacuum pump is operative to produce a flow rate of 20 to 40 microliters per minute across said functionalized card.

11. The sensor of claim 8 wherein said temperature control component is operative to stabilize the temperature of said functionalized card to within 0.15 degrees C. over a sixty minute period.

* * * * *